United States Patent [19]
Kanjolia et al.

[11] Patent Number: 5,502,227
[45] Date of Patent: Mar. 26, 1996

[54] LIQUID INDIUM SOURCE

[75] Inventors: Ravindra K. Kanjolia, North Andover; Benjamin C. Hui, Peabody, both of Mass.

[73] Assignee: CVD, Incorporated, Woburn, Mass.

[21] Appl. No.: 97,821

[22] Filed: Jul. 27, 1993

[51] Int. Cl.$^6$ ............................................. C07F 5/00
[52] U.S. Cl. ............................................................. 556/1
[58] Field of Search .................................................... 556/1

[56] References Cited

U.S. PATENT DOCUMENTS 4,720,560  1/1988  Hui et al. .................................... 556/1

Primary Examiner—José G. Dees
Assistant Examiner—Porfirio Nazario-Gonzalez
Attorney, Agent, or Firm—Wayne E. Nacker; Gerald K. White

[57] ABSTRACT

A uniform dosimetry of vapor phase trimethylindium is provided by dissolving trimethylindium in a $C_3$–$C_5$ trialkylindium and bubbling an inert carrier gas through the solution.

3 Claims, No Drawings

LIQUID INDIUM SOURCE

The present invention is directed to a method of providing a uniform dosimetry of vapor phase trimethylindium for epitaxial growth processes, such as metalorganic chemical vapor deposition (MOCVD).

BACKGROUND OF THE INVENTION

The most commonly used indium compound for MOCVD or other epitaxial deposition processes is trimethylindium. Materials produced by epitaxial growth using trimethylindium as an indium source include, for example InP, InGaAs, InGaAlP, InGaAsP, InGaAs/GaAs/AlGaAs, InAs, InSb and InAsBi.

A well-known inherent disadvantage of trimethylindium as an indium source is the fact that it is a solid at room temperature. Liquid sources of organometallic vapors are preferred to solid sources because a gas stream having a substantially constant partial pressure of organometallic vapors can be produced merely by bubbling carrier gas through the liquid at a constant rate. With solids, on the other hand, the surface area is constantly changing as the organometallic source is vaporized. Furthermore, solids, such as trimethylindium, tend to recondense on surfaces of the gas pathway, further increasing the difficulty of providing a uniform partial pressure of the organometallic compound.

Trimethylindium, being a solid, is an anomaly relative to other trialkylindiums, as $C_2$–$C_5$ alkylindiums are liquids at room temperature. This anomaly is the result of trimethylindium existing as a tetramer at room temperature, whereas other trialkylindiums are monomers. However, from the standpoint of providing a sufficiently high vapor pressure for epitaxial growth applications, trimethylindium, having a relatively high vapor pressure, tends to be preferred.

Several approaches have been taken to eliminate complications due to uneven mass flow when using trimethylindium. Some of these include reverse flow of carrier gas through the bubbler; packing the trimethylindium in inert material, such as Teflon beads, in the bubbler; use of two or more trimethylindium bubblers in series; and "solution trimethylindium" where the trimethylindium is dissolved and/or suspended in a high boiling amine or high boiling hydrocarbon.

Those approaches in which the trimethylindium remains in solid phase, reduce, but do not eliminate, uneven mass flow.

While trimethylindium may be dissolved in amine, its solubility is low, typically about 20%, requiring a large volume of trimethylindium source. Amines complex with trimethylindium, advantageously breaking up the tetramer, but disadvantageously tying up trimethylindium. Because epitaxial growth applications require a source with very minimal high vapor pressure impurities, amine solvents are used which are highly purified, particularly with respect to volatile impurities. Nevertheless, if impurities are present, they may react with the trimethylindium, producing new, more volatile impurities. Also, even high boiling amines are entrained in the gas stream to some extent and may undesirably introduce nitrogen into the material which is being produced.

High boiling hydrocarbons avoid the problem of nitrogen. However, trimethylindium is even less soluble in hydrocarbons than amines, and the trimethylindium is more dispersed than dissolved in hydrocarbon media. Because hydrocarbons do not break up the tetramer, problems with deposition of trimethylindium in the gas pathway remain. Also, as with amines, there is the possibility that impurities will react with trimethylindium to produce volatile impurities.

U.S. Pat. No. 4,720,560 approaches the problem by mixing two moles of trimethylindium with a mole of triethylindium to produce ethyldimethylindium by the reversible reaction:

$$2\ Me_3In + Et_3In \rightarrow 3\ EtMe_2In.$$

The desired indium source in this approach is not trimethylindium, but ethyldimethylindium. Because the equilibrium is temperature-dependent with the equilibrium shifting to the right at lower temperatures, it is advised to maintain the mixture at a temperature below room temperature, e.g., at about 10° C. Such a lowered temperature may be disadvantageous if high vapor pressures are required for the crystal growth. Increasing the temperature may potentially cause the above equilibrium to shift to the left, and cause the ethyldimethylindium to dispreportionate.

SUMMARY OF THE INVENTION

In accordance with the invention, a liquid source of indium comprises trimethylindium dissolved in a $C_3$–$C_5$ trialkylindium or mixture of $C_3$–$C_5$ trialkylindiums. Gas, such as hydrogen or helium, bubbled through this source entrains trimethylindium in monomeric form.

DETAILED DESCRIPTION OF CERTAIN PREFERRED EMBODIMENTS

Trimethylindium is highly soluble in high-boiling trialkylindiums, such as $C_3$–$C_5$ trialkylindiums. As is the case with the trimethylindium/triethylindium system, it is believed that a reversible reaction occurs when trimethylindium is introduced into a higher trialkylindium:

$Me_3In + (C_3-C_5 alkyl)_3In \rightarrow Me_x(C_3-C_5 alkyl)_{(3-x)}In$; where $x = 1$ or 2. Thus, up to two moles of trimethylindium can be dissolved into 1 mole of $C_3$–$C_5$ trialkylindium. For example, 320 grams of trimethylindium may be dissolved into 286 grams of tributylindium.

Although tripropylindiums may be used as solvents, butylindiums, such a tri n-butylindium (b.p. 85°–6° C./0.1 mm Hg) and triisobutylindium (b.p. 71°–2° C./0.05 mm Hg) (or mixtures of these isometric tributylindiums) are preferred because of their higher boiling point. The solvents are preferably highly purified, e.g., to five 9's purity. An advantage of trialkylindiums as solvents for trimethylindium, relative to amines or hydrocarbons, are that any trace impurities, which in the case of the amine or hydrocarbon might react with trimethylindium to produce volatile impurities, would have already reacted with the higher trialkylindium to produce either a non-volatile impurity or a volatile impurity which would be removed in the purification process. Also, unlike amines which might introduce nitrogen into the material being deposited, the higher trialkylindiums introduce no element in addition to those present in trimethylindium. Like amine solvents, trialkylindium solvents break the tetrameric trimethylindium into monomeric form, which is the form that is vaporized.

Unlike the trimethylindium/triethylindium system described in U.S. Pat. No. 4,720,560, essentially the only volatile species is trimethylindium. Also, at higher temperatures, where a higher vapor pressure of trimethylindium is achieved, the equilibrium shifts to the left, enhancing the amount of trimethylindium available for entrainment by the carrier gas. As a result, the bubbler may be maintained at higher temperatures, 17°–40° C. being a typical temperature for the bubbler. As a consequence of there being a single volatile species which is constantly replenished by the equilibrium of the reaction, the amount of trimethylindium entrained by a carrier gas tends to be very constant over time, until trimethylindium is substantially depleted, whereupon a rather sharp drop-off may occur. By depositing in the trimethylindium concentration range where the mass flow of trimethylindium is constant, more uniform epitaxial growth may be achieved.

To provide the most constant mass flow of trimethylindium, it is advantageous to initially provide a saturated or nearly saturated solution of trimethyl indium.

Suitable carrier gasses are those which are non-reactive with the trimethyl indium or with the trialkylindium solvent. Hydrogen is the preferred carrier gas, but other gases, such as helium or argon may be used.

What is claimed is:

1. A method of providing vapor phase trimethylindium comprising dissolving trimethylindium in a $C_3$–$C_5$ trialkylindium solvent to produce a solution and entraining trimethylindium from said solution with a carrier gas.

2. A method according to claim 1 wherein said solvent is selected from the group consisting of tri n-butylindium, triisobutylindium and mixtures thereof.

3. A method according to claim 1 wherein said trimethylindium is dissolved at a molar ratio relative to said solvent of at least about 0.05.

* * * * *